US007956083B2

(12) United States Patent
Johnson et al.

(10) Patent No.: US 7,956,083 B2
(45) Date of Patent: Jun. 7, 2011

(54) COMPOUNDS

(75) Inventors: Christopher Norbert Johnson, Harlow (GB); David G. Jones, Durham, NC (US); Xi Liang, Durham, NC (US); David Timothy MacPherson, Harlow (GB); Aaron B Miller, Durham, NC (US); Steven James Stanway, Harlow (GB); Andrew Kenneth Takle, Harlow (GB); Giancarlo Trani, Harlow (GB); Antoinette Wilson, Harlow (GB)

(73) Assignee: Glaxo Group Limited, Greenford, Middlexsex (GB)

( * ) Notice: Subject to any disclaimer, the term of this patent is extended or adjusted under 35 U.S.C. 154(b) by 0 days.

(21) Appl. No.: 12/864,933

(22) PCT Filed: Feb. 17, 2009

(86) PCT No.: PCT/EP2009/051875
§ 371 (c)(1),
(2), (4) Date: Jul. 28, 2010

(87) PCT Pub. No.: WO2009/103710
PCT Pub. Date: Aug. 27, 2009

(65) Prior Publication Data
US 2010/0324106 A1    Dec. 23, 2010

(30) Foreign Application Priority Data

Feb. 19, 2008  (GB) .................................. 0803017.3

(51) Int. Cl.
*A01N 43/38* (2006.01)
*C07D 209/04* (2006.01)
(52) U.S. Cl. ....................................... 514/415; 548/511
(58) Field of Classification Search ........................ None
See application file for complete search history.

(56) References Cited

FOREIGN PATENT DOCUMENTS
| WO | 2005018636 A1 | 3/2005 |
| WO | 2006040351 A1 | 4/2006 |
| WO | 2008107455 A1 | 9/2008 |

OTHER PUBLICATIONS

Collins, Expert Opinion Investig Drugs (2007), 16(11), p. 1743-1751.*
FR5142, caplus an 1970:66812.*

* cited by examiner

*Primary Examiner* — Sun Jae Y Loewe
(74) *Attorney, Agent, or Firm* — J. Scott Young

(57) ABSTRACT

The present invention relates to novel indole derivatives having pharmacological activity, processes for their preparation, compositions containing them and the use of these compounds in the treatment of estrogen receptor beta mediated diseases.

3 Claims, No Drawings

COMPOUNDS

CROSS-REFERENCE TO RELATED APPLICATIONS

This application is filed pursuant to 35 USC 371 as a United States National Phase Application of International Patent Application Serial No. PCT/EP2009/051875 filed on Feb. 17, 2009, which claims priority from 0803017.3 filed on Feb. 19, 2008 in the United Kingdom.

FIELD OF THE INVENTION

The present invention relates to novel indole derivatives having pharmacological activity, processes for their preparation, compositions containing them and the use of these compounds in the treatment of estrogen receptor beta mediated diseases.

BACKGROUND OF THE INVENTION

Estrogens are well-known endocrine regulators in the cellular processes involved in the development and maintenance of the reproductive system. Estrogens have also been shown to have important effects in many non-reproductive tissues such as bone, liver, the cardiovascular system, and the central nervous system. Estrogen receptors are ligand-activated transcription factors and belong to the nuclear hormone receptor subfamily. Upon binding ligand, these receptors dimerize and can activate gene transcription either by directly binding to specific sequences on DNA known as response elements or by interacting with transcription factors (such as AP1) which in turn bind directly to specific DNA sequences. Additionally, it is now becoming apparent that estrogens may mediate their effects via kinase-mediated signalling cascade, though much of this work is still experimental. Kousteni et al., *Journal of Clinical Investigation*, (2003), 111, 1651-1664, herein incorporated by reference with regard to such teaching.

Historically estrogens were believed to manifest their biological activity through a single estrogen receptor, now termed estrogen receptor alpha (ERα). More recently, however, there was the discovery of second subtype of estrogen receptor, termed estrogen receptor beta (ERβ or ER beta). See, Kuiper et al., WO 97/09348 and Kuiper et al., *Cloning of a Novel Estrogen Receptor Expressed in Rat Prostate and Ovary*, Proc. Natl. Acad. Sci. U.S.A., 1996, pp. 5925-5930. ERβ is expressed in humans. See, Mosselman et al., ERβ: *Identification and Characterization of a Novel Human Estrogen Receptor*, FEBR S Lett., 1996, pp. 49-53. The discovery of this second subtype of estrogen receptor significantly increased the biological complexity of estrogen signalling.

The tissue distribution of ERβ has been well mapped in the rodent and it is not coincident with ERα. Tissues such as the mouse uterus express predominantly ERα, whereas the mouse lung express predominantly ERβ [Couse, et al., Endocrinology 138: 4613-4621 (1997), Kuiper, et al., Endocrinology 138: 863-870 (1997)]. Even within the same organ, the distribution of ERα and ERβ can be compartmentalized. For example, in the rat ovary, ERβ is highly expressed in the granulosa cells and ERα is restricted to the thecal and stromal cells [Sar and Welsch, Endocrinology 140: 963-971 (1999)]. However, there are examples where the receptors are coexpressed and there is evidence of in vitro studies that ERα and ERβ can form heterodimers [Cowley, et al., Journal of Biological Chemistry 272: 19858-19862 (1997)].

The most potent endogenous estrogen is 17β-estradiol. A large number of compounds have been described that either mimic or block the activity of 17β-estradiol. Compounds having roughly the same biological effects as 17β-estradiol are referred to as "estrogen receptor agonists". Those which block the effects of 17β-estradiol, when given in combination with it, are called "estrogen receptor antagonists". In reality, there is a continuum between estrogen receptor agonist and estrogen receptor antagonist activity and some compounds behave as estrogen receptor agonists in some tissues but estrogen receptor antagonists in others. Compounds with mixed activity are called selective estrogen receptor modulators (SERMS) and may be therapeutically useful agents. The precise reason why the same compound can have cell-specific effects has not been elucidated, but the differences in receptor conformation and/or in the milieu of coregulatory proteins have been suggested.

DESCRIPTION OF THE INVENTION

The compounds of the invention bind to the ERβ nuclear receptor and may therefore useful in treating ERβ mediated diseases for example the compounds of this invention may be useful in the treatment of pain, chronic inflammatory disorders, autoimmune diseases, CNS disorders, metabolic disorders or appetite disorders. The compounds of the invention may be cardioprotective. The compounds of this invention may also be useful in treating or inhibiting benign or malignant abnormal tissue growth, and given that the compounds in this invention are estrogen receptor agonists they may also be useful in the treatment of disorders or conditions at least partially mediated by estrogen deficiency.

The present invention provides, in a first aspect, compounds of formula (I):

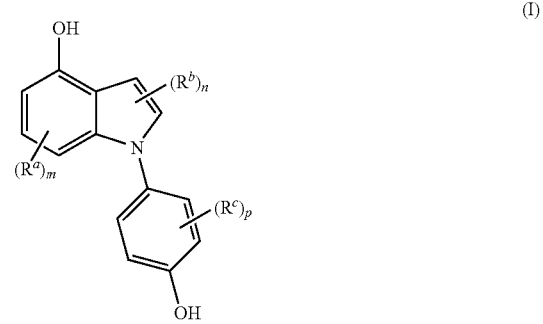

wherein $R^a$, $R^b$ and $R^c$ are independently selected from halo, $C_{1-4}$alkoxy, $C_{1-4}$alkyl, $C_{2-4}$alkenyl, $C_{1-5}$alkanoyl, $CF_3$, $CF_3O$ and cyano;

m is zero or an integer from 1 to 3;
n is zero or an integer 1 or 2;
p is zero or an integer from 1 to 4;
however m, n and p together equal 5 or less;
or a salt thereof.

The term '$C_{1-4}$ alkyl' as used herein as a group or a part of the group refers to a linear or branched saturated hydrocarbon group containing from 1 to 4 carbon atoms. Examples of such groups include methyl, ethyl, n-propyl, isopropyl, n-butyl, isobutyl, sec-butyl and tert-butyl and the like.

The term '$C_{2-4}$ alkenyl' as used herein as a group or a part of the group refers to a linear or branched unsaturated hydrocarbon group containing from 2 to 4 carbon atoms and one double bond. Examples of such groups include ethenyl, 1-prop-2-enyl, 2-prop-2-enyl and the like.

The term 'C$_{1-4}$ alkoxy' as used herein refers to an —O—C$_{1-4}$ alkyl group wherein C$_{1-4}$alkyl is as defined herein. Examples of such groups include methoxy, ethoxy, propoxy or butoxy and the like.

The term 'C$_{1-5}$alkanoyl' as used herein refers to a —COH or —COC$_{1-4}$alkyl group wherein C$_{1-4}$alkyl is as defined herein.

The term 'halo' as used herein refers to a fluoro, chloro, bromo or iodo atom.

In one embodiment, m is 0, 1 or 2.

In one embodiment, n is 0 or 1, particularly 0.

In one embodiment, p is 0, 1 or 2.

In one embodiment, m is 1, n is 0 and p is 1. In another embodiment, m is 2, n is 0 and p is 1. In another embodiment, m is 0, n is 0 and p is 1. In another embodiment, m is 0, n is 1 and p is 1. In another embodiment, m is 1, n is 0 and p is 0. In another embodiment, m is 0, n is 0 and p is 2. In a further embodiment, m is 0, n is 0 and p is 0.

In one embodiment, R$^a$ is independently selected from halo, C$_{1-4}$ alkyl and cyano. In another embodiment, R$^a$ is independently selected from fluoro, bromo, chloro, ethyl and cyano. In a particular embodiment, R$^a$ is independently selected from fluoro, bromo and cyano. In one embodiment, R$^a$ is cyano.

In one embodiment, R$^b$ is a C$_{1-4}$ alkyl group. In a particular embodiment, R$^b$ is methyl.

In one embodiment, R$^c$ is halo, in particular fluoro.

In one embodiment n is 1.

In one embodiment R$^c$ is ortho to the hydroxy group on the phenyl ring.

In one embodiment R$^a$ is on the C6 position on the indole.

In one embodiment, m is 1, n is 0 and p is 1, R$^c$ is fluoro and ortho to the hydroxy group on the phenyl ring, R$^a$ is selected from halo, C$_{1-4}$ alkyl and cyano, particularly fluoro, chloro, ethyl and cyano.

In one embodiment, m is 1, n is 0 and p is 0, R$^a$ is selected from halo, particularly fluoro.

In one particular embodiment, a compound of formula (I) or a salt thereof is selected from a compound of Examples 1 to 14, or a salt thereof.

It is to be understood that the present invention encompasses all isomers of formula (I) and their salts including all geometric and optical forms, and mixtures thereof (e.g. racemic mixtures). Where additional chiral centres are present in compounds of formula (I), the present invention includes within its scope all possible stereoisomers, including mixtures thereof. The different isomeric forms may be separated or resolved one from the other by conventional methods, or any given isomer may be obtained by conventional synthetic methods or by stereospecific or asymmetric syntheses.

The present invention may also include isotopically-labelled compounds, which are identical to the compounds of formula (I), except that one or more atoms are replaced by an atom having an atomic mass or mass number different from the atomic mass or mass number usually found in nature. Examples of isotopes that may be incorporated into compounds of the invention include isotopes of hydrogen, carbon, nitrogen, oxygen, phosphorous, fluorine, iodine, and chlorine, such as 2H, $^3$H, $^{11}$C, $^{14}$C, $^{18}$F, $^{35}$S, $^{123}$I and $^{125}$I. Compounds of the present invention and salts of said compounds that contain the aforementioned isotopes and/or other isotopes of other atoms are within the scope of the present invention. Isotopically-labelled compounds of the present invention, for example those into which radioactive isotopes such as $^3$H and/or $^{14}$C are incorporated, are useful in drug and/or substrate tissue distribution assays. $^3$H and $^{14}$C are considered useful due to their ease of preparation and detectability. $^{11}$C and $^{18}$F isotopes are considered useful in PET (positron emission tomography), and $^{125}$I isotopes are considered useful in SPECT (single photon emission computerized tomography), and all are considered useful in brain imaging. Substitution with heavier isotopes such as $^2$H may afford certain therapeutic advantages resulting from greater metabolic stability, for example increased in vivo half-life or reduced dosage requirements and, hence, are considered useful in some circumstances. In one embodiment, the compounds of formula (I) or salts thereof are not isotopically labelled.

It will be appreciated that certain compounds of formula (I), or their salts, may exist as solvates, such as hydrates. Where solvates exist, this invention includes within its scope stoichiometric and non-stoichiometric solvates.

It will be appreciated that certain compounds of formula (I), or their salts, may exist in more than one polymorphic form. The invention extends to all such forms whether in a pure polymorphic form or when admixed with any other material, such as another polymorphic form.

Because of the potential use of compounds of formula (I) in medicine, salts of compounds of formula (I) are preferably pharmaceutically acceptable.

Pharmaceutically acceptable salts include those described by Berge, Bighley and Monkhouse, *J. Pharm. Sci.*, 1977, 66, 1-19. The term "pharmaceutically acceptable salts" refers to salts prepared from pharmaceutically acceptable bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic bases include salts of primary, secondary, and tertiary amines; substituted amines including naturally occurring substituted amines; and cyclic amines. Particular pharmaceutically acceptable organic bases include arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, procaine, purines, theobromine, triethylamine, trimethylamine, tripropylamine, tris(hydroxymethyl)aminomethane (TRIS, trometamol) and the like. Salts may also be formed from basic ion exchange resins, for example polyamine resins.

Compounds of formula (I) can be prepared as set forth in the following Schemes and in the examples. The following processes form another aspect of the present invention.

Processes for the preparation of compounds of formula (I) comprise;

(a) reaction of a compound of formula (IIa) or (IIb),

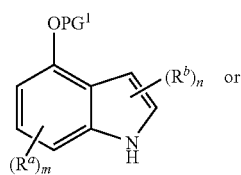

(IIa)

-continued

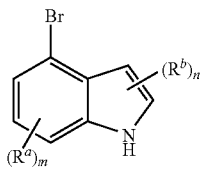
(IIb)

wherein $R^a$, $R^b$, m and n are as defined for compounds of formula (I) and $PG^1$ represents a protecting group such as methyl or an optionally substituted benzyl group, with a compound of formula (IIIa) or (IIIb), or a protected derivative thereof

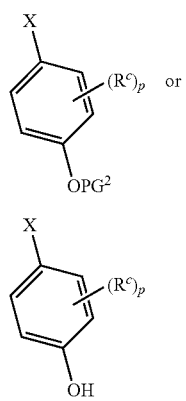

wherein $R^c$ and p are as defined above, $PG^2$ represents a protecting group such as methyl or an optionally substituted benzyl group and X represents a leaving group such as halo (e.g. bromo or iodo) or a residue such as —B(OH)$_2$ or an equivalent boronate ester, and thereafter removing any protecting groups $PG^1$ and $PG^2$; and in case of a reaction of a compound of formula (IIb) substituting the bromo group in the 4-position with a hydroxy group; or (b) interconversion of compounds of formula (I) or protected derivatives thereof; or (c) deprotection of a compound of formula (I) which is protected; or (d) as appropriate, separation of diastereomeric or enantiomeric mixtures of compounds of formula (I) and/or formation of a salt thereof; and (e) optionally preparing a salt of a compound of formula (I).

Reactions of compounds of formula (IIa) or (IIb) with compounds of formula (IIIa) or (IIIb) according to process (a) are typically carried out in the presence of a transition metal salt such as a copper halide, an appropriate base such as potassium phosphate, potassium carbonate or triethylamine and, optionally, a suitable coordinating ligand such as a 1,2-diamine (e.g 1,2-(dimethylamino)cyclohexane or an amino acid. Where X represents a leaving group such as halo, use of a copper (I) source is advantageous, such as copper (I) iodide, in the presence of a base such as potassium phosphate or potassium carbonate optionally in the presence of a ligand such as a 1,2-diamine (e.g. 1,2-(dimethylamino)cyclohexane) or an amino acid (e.g. proline). Suitable solvents for this reaction are for example toluene, dichloromethane, dimethylsulfoxide, N,N-dimethylformamide, N-methyl-2-pyrrolidinone and 1,4-dioxane. Where X represents a residue such as —B(OH)$_2$ or an equivalent boronate ester, a source of copper (II) may be employed, such as copper (II) acetate in the presence of a base such as triethylamine or pyridine using a suitably inert solvent such as dichloromethane. Reactions according to process (a) may be carried out at ambient temperature or elevated temperature e.g. under reflux or using microwave radiation and optionally in the presence of molecular sieves.

In process (a), in the case of a reaction of a compound of formula (IIb), substitution of the bromo group in the 4-position is typically carried out via the addition of a suitable hydroxide salt such as potassium hydroxide and treatment with a suitable phosphine ligand, for example 2-di-tert-butylphosphino-2',4',6'-triisopropylbiphenyl, in the presence of a suitable catalyst such as Pd$_2$(dba)$_2$. This may be carried out in a suitable solvent or solvent mixture such as a dioxane/water=1/1 mixture at a suitable temperature, for example 85 and 90° C.

In processes (a) and (c), examples of protecting groups and the means for their removal can be found in T. W. Greene 'Protective Groups in Organic Synthesis' (J. Wiley and Sons, 1991). For example an optionally substituted benzyl group may be removed by hydrogenolysis. e.g in the presence of 10% Pd on charcoal.

Separations according to process (d) may be carried out using established methodology, e.g. by chromatography, resolution as diastereomeric salts or crystallisation.

Compounds of formula (II) and (III) are known in the literature or can be prepared by analogous methods.

It will be appreciated that compounds of formulas (II) and (III) may be obtained as mixtures of diastereomers and/or enantiomers. Such mixtures may optionally be separated using established methodology, e.g. by chromatography.

The term "protected derivative thereof" is used herein to refer to compound which includes a protecting group for example those referred to above.

The compounds of the invention bind to the ERβ nuclear receptor and may therefore useful in treating ERβ mediated diseases.

In one embodiment compounds of the invention are selective for ERβ over ERα, e.g. in one embodiment compounds of the invention may have greater than 5 fold higher affinity at ERβ compared to ERα.

In view of their ability to bind to the ERβ nuclear receptor, the compounds of this invention may be useful in the treatment of the disorders that follow.

The compounds of the formula may be useful in the treatment of pain.

When used herein the term pain, includes acute pain, chronic pain, chronic articular pain, musculoskeletal pain, inflammatory pain, visceral pain, pain associated with cancer, pain associated with migraine, tension headache and cluster headaches, pain associated with functional bowel disorders, lower back and neck pain, pain associated with sprains and strains, sympathetically maintained pain; myositis, pain associated with influenza or other viral infections such as the common cold, pain associated with rheumatic fever, pain associated with myocardial ischemia, post operative pain, headache, toothache and dysmenorrhea.

In one embodiment the compounds may be useful in the treatment of chronic pain, post-operative pain, chronic lower back and neck pain, cancer pain, sprains and strains.

Chronic articular pain conditions include rheumatoid arthritis, osteoarthritis, rheumatoid spondylitis, gouty arthritis and juvenile arthritis.

Pain associated with functional bowel disorders includes non-ulcer dyspepsia, non-cardiac chest pain and irritable bowel syndrome.

The compounds of the invention may be also useful in the treatment of chronic inflammatory disorders or autoimmune diseases including arthritis, (rheumatoid, osteoarthritis and spondyloarthropathies), inflammatory bowel disease (Crohn's disease, ulcerative colitis, indeterminate colitis), multiple sclerosis, diabetes, ischemia/reperfusion injury, psoriasis, sepsis, systemic lupus erythematosus and endometriosis.

The compounds of this invention may be cardioprotective and useful for the treatment of hypercholesteremia, atherosclerosis, cardiovascular disease, hyperlipidemia and immune cell mediated vascular damage.

The compounds of this invention may also be useful in treating benign or malignant abnormal tissue growth including prostatic hypertrophy, breast cancer, colon cancer and prostate cancer.

Compounds exhibiting ERβ receptor binding activity have been described to have activity in brain and therefore may be useful for inhibiting or treating CNS disorders including depression, anxiety, insomnia, schizophrenia, Alzheimer's disease, cognitive decline, senile dementia and neurodegenerative disorders.

As compounds of the invention are estrogen receptor agonists they may be useful in the treatment of disorders or conditions at least partially mediated by estrogen deficiency. In particular, these compounds may be useful for the treatment of menopausal and post-menopausal disorders (vasomotor symptoms, urogenital or vulvar vaginal atrophy, atrophic vaginitis, female sexual dysfunction, bone demineralization and the treatment of osteoporosis.

Additional indications include metabolic disorders such as type II diabetes and appetite disorders (obesity).

When used herein the term "treatment" extends to prophylaxis of the above disorders as well as treatment of established conditions, e.g. inhibition of benign or malignant abnormal tissue, prophylaxis of menopausal and post-menopausal disorders, osteoporisis and osteoarthritis.

Thus the invention also provides a compound of formula (I) or a salt thereof, for use as a cardioprotective therapy or as a therapeutic substance in the treatment of the above disorders, in particular pain, chronic inflammatory disorders, autoimmune diseases, benign or malignant abnormal tissue growth, CNS disorders, metabolic disorders, appetite disorders, disorders or conditions at least partially mediated by estrogen deficiency.

The invention further provides a method of treatment of the above disorders, in mammals including humans, which comprises administering to the sufferer a therapeutically effective amount of a compound of formula (I) or a salt thereof.

In another aspect, the invention provides the use of a compound of formula (I) or a salt thereof in the manufacture of a medicament for use in the treatment of the above disorders.

When used in therapy, the compounds of formula (I) are usually formulated in a standard pharmaceutical composition. Such compositions can be prepared using standard procedures.

Thus, the present invention further provides a pharmaceutical composition for use in the treatment of the above disorders which comprises the compound of formula (I) or a salt thereof and a pharmaceutically acceptable carrier.

The present invention further provides a pharmaceutical composition which comprises the compound of formula (I) or a salt thereof and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms may be prepared utilising a compound of the invention or a salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.01% to 99% by weight, preferably from 1 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three a day. Such therapy may extend for a number of weeks or months.

A further aspect to the invention is a pharmaceutical composition comprising 0.05 to 1000 mg of a compound of formula (I) or a pharmaceutically acceptable salt thereof, and 0 to 3 g more suitably 0 to 2 g of at least one pharmaceutically acceptable carrier.

The precise amount of the compounds of formula (I) administered to a host, particularly a human patient, will be the responsibility of the attendant physician. However, the dose employed will depend on a number of factors including the age and sex of the patient, the precise condition being treated and its severity, and the route of administration.

A compound of formula (I) or a pharmaceutically acceptable salt thereof may be used in combination with other therapeutic agents.

The compounds of the invention may be used in combination with other therapeutic agents, for example COX-2 (cyclooxygenase-2) inhibitors, such as celecoxib, deracoxib, rofecoxib, valdecoxib, parecoxib, COX-189 or 2-(4-ethoxyphenyl)-3-(4-methanesulfonyl-phenyl)-pyrazolo[1,5-b]pyridazine (WO99/012930); 5-lipoxygenase inhibitors; NSAIDs (non-steroidal anti-inflammatory drugs) such as diclofenac, indomethacin, nabumetone or ibuprofen; bisposphates, leukotriene receptor antagonists; DMARDs (disease modifying anti-rheumatic drugs) such as methotrexate; adenosine A1 receptor agonists; sodium channel blockers, such as lamotrigine; NMDA (N-methyl-D-aspartate) receptor modulators, such as glycine receptor antagonists; ligands for the $\alpha_2\delta$-subunit of voltage gated calcium channels, such as gabapentin and pregabalin; tricyclic antidepressants such as amitriptyline; neurone stabilising antiepileptic drugs; mono-aminergic uptake inhibitors such as venlafaxine; opioid analgesics; local anaesthetics; $5HT_1$ agonists, such as triptans, for example sumatriptan, naratriptan, zolmitriptan, eletriptan, frovatriptan, almotriptan or rizatriptan; nicotinic acetyl choline (nACh) receptor modulators; glutamate receptor modulators, for example modulators of the NR2B subtype; $EP_4$ receptor ligands; $EP_2$ receptor ligands; $EP_3$ receptor ligands; $EP_4$ agonists and $EP_2$ agonists; $EP_4$ antagonists; $EP_2$ antagonists and $EP_3$ antagonists; cannabanoid receptor ligands; bradykinin receptor ligands; vanilloid receptor ligand; and purinergic receptor ligands, including antagonists at $P2X_3$, $P2X_{2/3}$, $P2X_4$, $P2X_7$ or $P2X_{4/7}$. When the compounds are used in combination with other therapeutic agents, the compounds may be administered either sequentially or simultaneously by any convenient route.

Additional COX-2 inhibitors are disclosed in U.S. Pat. No. 5,474,995 U.S. Pat. No. 5,633,272; U.S. Pat. No. 5,466,823, U.S. Pat. No. 6,310,099 and U.S. Pat. No. 6,291,523; and in WO 96/25405, WO 97/38986, WO 98/03484, WO 97/14691, WO99/12930, WO00/26216, WO00/52008, WO00/38311, WO01/58881 and WO02/18374.

Other therapeutic agents claimed to be useful as either disease modifying or symptomatic treatments of Alzheimer's disease may be used in combination with the compounds of the present invention. Suitable examples of such other therapeutic agents may be agents known to modify cholinergic transmission such as $5\text{-}HT_{1A}$ antagonists, (e.g. lecozotan), 5-HT6 antagonists, M1 muscarinic agonists, M2 muscarinic antagonist, acetylcholinesterase inhibitors (e.g donepezil or rivastigmine), or allosteric modulators, nicotinic receptor agonists or allosteric modulators, symptomatic agents such as 5-HT6 receptor antagonists, H3 receptor antagonists, 5HT4 receptor agonist, also NMDA receptor antagonists or modulators, and disease modifying agents such as β or γ-secretase inhibitors (e.g. R-flurbiprofen). Other suitable examples of such other therapeutic agents may be medicaments claimed to be useful in the treatment of pain of neuropathic origin including neuralgias, neuritis and back pain, and inflammatory pain including osteoarthritis, rheumatoid arthritis, acute inflammatory pain, back pain and migraine.

When the compounds are used in combination with other therapeutic agents, the compounds may be administered either sequentially or simultaneously by any convenient route.

The invention thus provides, in a further aspect, a combination comprising a compound of formula (I) or a pharmaceutically acceptable salt thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable salt thereof is used in combination with a second therapeutic agent active against the same disease state the dose of each compound may differ from that when the compound is used alone. Appropriate doses will be readily appreciated by those skilled in the art.

All publications, including but not limited to patents and patent applications, cited in this specification are herein incorporated by reference as if each individual publication were specifically and individually indicated to be incorporated by reference herein as though fully set forth.

The following non-limiting Examples illustrate the preparation of pharmacologically active compounds of the invention.

EXAMPLES

In the procedures that follow, after each starting material, reference to a description is typically provided. This is provided merely for assistance to the skilled chemist. The starting material may not necessarily have been prepared as described in the description referred to.

LC/Mass Spectra were Obtained Using Either a

5 Minute Method

Agilent 1100 series HPLC system coupled with a Waters ZQ Mass Spectrometer. LC analysis was performed on a Waters Atlantis column (50×4.6 mm, 3μm) (mobile phase: 97% [water+0.05% $HCO_2H$]/3% [$CH_3CN$+0.05% $HCO_2H$] for 0.1 min, then a gradient to 3% [water+0.05% $HCO_2H$]/ 97% [$CH_3CN$+0.05% $HCO_2H$] over 3.9 min, and then held under these conditions for 0.8 min); temperature=30° C.; flow rate=3 mL/min; Mass spectra were collected using electrospray and/or APCI. In the mass spectra only one peak in the molecular ion cluster is reported. The UV detection range is from 220 to 330 nm.

Or a 2 Minute Method

Hardware: Waters Acquity Binary solvent Manager, Waters Acquity Sample Manager, Waters Acquity Column Oven, Waters Acquity Photo Diode Array, Waters ZQ Mass Spectrometer, Polymer Labs ELSD PL1000, Computer System. XP SP2

Software: Waters MassLynx v4.1

Column: Acquity UPLC BEH $C_{18}$ 1.7 μm 2.1 mm×50 mm, column oven set to 40 degrees centigrade Solvents: A-Aqueous solvent=Water 0.1% Formic Acid+ 10 mM Ammonium Acetate, B-Organic solvent=MeCN: Water 95:5+0.05% Formic Acid Instrument settings: Injection volume: 0.5 μl, UV detection: 220 to 330 nm, MS scan range: 100 to 1000 amu, MS scanning rate: 0.2 second scan with a 0.1 second inter scan delay, MS scan function: Electrospray with pos neg switching Gradient:

| Time | Flow ml/min | % A | % B |
|---|---|---|---|
| 0 | 1 | 97 | 3 |
| 0.1 | 1 | 97 | 3 |
| 1.4 | 1 | 0 | 100 |
| 1.9 | 1 | 0 | 100 |
| 2 | 1 | 97 | 3 |

Proton Magnetic Resonance (NMR) spectra were recorded on a Bruker instrument at 250 or 400 MHz. Chemical shifts are reported in ppm (δ) using tetramethylsilane as internal standard. Splitting patterns are designated as s, singlet; d, doublet; t, triplet; q, quartet; m, multiplet; br, broad. The NMR spectra were recorded at a temperature ranging from 25 to 90° C. When more than one conformer was detected the chemical shifts for the most abundant one are reported.

Chromatography was carried out on silica gel cartridges either on a Flashmaster II (Argonaut) or a Biotage SP4 automated chromatography system and an appropriate elution solvent system.

Mass Directed Automated Preparative (MDAP) HPLC instruments consist of the following: Waters 2525 Binary Gradient Module, Waters 515 Makeup Pump, Waters Pump Control Module, Waters 2767 Inject Collect, Waters Column Fluidics Manager, Waters 2996 Photodiode Array Detector, Waters ZQ Mass Spectrometer, Gilson 202 fraction collector, Gilson Aspec waste collector. Column: Waters Atlantis, dimensions are 19 mm×100 mm (<100 mg scale) and 30 mm×100 mm (>100 mg scale), particle size is 5 μm. Solvents, A: Aqueous solvent=Water+0.1% Formic Acid B: Organic solvent=Acetonitrile+0.1% Formic Acid. Gradients range from 5-30% B in A to 80-99% B in A, depending on HPLC retention time, run time=13.5 minutes. Flow rate=20 ml/min (<100 mg scale), 40 ml/min (>100 mg scale)

The H-Cube™ is a continuous flow hydrogenation instrument manufactured by THALES Inc (Budapest)

ABBREVIATIONS

DMF—N,N-Dimethylformamide
DCM—Dichloromethane
THF—Tetrahydrofuran
DME—Ethylene glycol dimethyl ether
$Pd_2dba_3$—Tris(dibenzylideneacetone)dipalladium (0)
AIBN—Azobisisobutyronitrile
Rf—Retention factor Description 1. 1-{3-Fluoro-4-[(phenylmethyl)oxy]phenyl}-4-[(phenylmethyl)oxy]-1H-indole (D1)

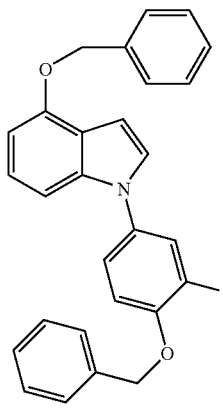

A mixture of 4-benzyloxyindole (3.35 g, 15 mmol), 4-bromo-2-fluoro-1-[(phenylmethyl)oxy]benzene (4.22 g, 15 mmol) and potassium phosphate (6.68 g, 31.5 mmol) in toluene (25 mL) was degassed by bubbling argon through the solution for 3 minutes. Copper (I) iodide (143 mg, 0.75 mmol) and (1S,2S)-N,N'-dimethyl-1,2-cyclohexanediamine (426 mg, 0.479 ml, 3.0 mmol) were added and the mixture was refluxed under argon for 24 hrs. After cooling, the mixture was filtered through a plug of silica gel (elution with ethyl acetate) and concentrated. Chromatography (2 columns, elution with 0-50% ethyl acetate in hexane and then a gradient of diethyl ether in hexane) gave the title compound (D1) 2.32 g.

LC-MS: MH$^+$=424 ($C_{28}H_{22}FNO_2$=423)

NMR (δ$_H$), (CDCl$_3$): 5.21 (2H, s), 5.26 (2H, s), 6.64 (1H, m), 6.83 (1H, d, J=3.2 Hz), 7.08-7.19 (5H, m), 7.28-7.53 (11H, m)

Description 2. 2-Fluoro-4-{3-methyl-4-[(phenylmethyl)oxy]-1H-indol-1-yl}phenol (D2)

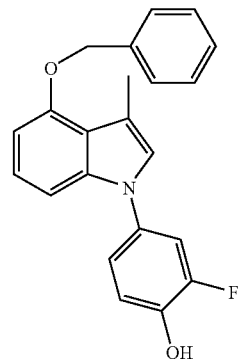

To a solution of 3-methyl-4-[(phenylmethyl)oxy]-1H-indole (R. A. Heacock et al. Canadian Journal of Chemistry, (1964), 42(3), 514) (617 mg, 2.60 mmol) in N-methyl-2-pyrrolidinone (10 mL) was added 4-bromo-2-fluorophenol (0.28 mL, 2.60 mmol), copper iodide (96 mg, 0.50 mmol) and potassium carbonate (867 mg, 6.28 mmol). The reaction mixture was heated in a Biotage Initiator™ Microwave Synthesizer at 190° C. for 3 hours. The mixture was filtered through a pad of Celite which was subsequently washed with ethyl acetate. The ethyl acetate solution was washed with water and then the aqueous layer re-extracted with ethyl acetate. The combined organic layers were dried over magnesium sulfate, filtered and then concentrated in vacuo. The product was purified by silica gel chromatography eluting with 0-30% ethyl acetate in hexane to yield the title compound (D2) (147 mg).

LC-MS: MH$^+$=348 ($C_{22}H_{18}FNO_2$=347)

Description 3. 2-Fluoro-4-{2-methyl-4-[(phenylmethyl)oxy]-1H-indol-1-yl}phenol (D3)

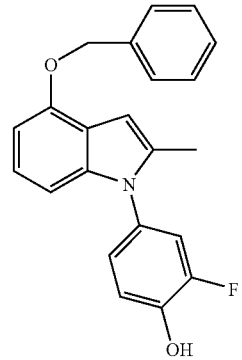

To a solution of 2-methyl-4-[(phenylmethyl)oxy]-1H-indole {WO9204321} (440 mg, 1.86 mmol) in N-methyl-2-pyrrolidinone (4 mL) was added 4-bromo-2-fluorophenol (0.205 mL, 1.87 mmol), copper iodide (70 mg, 0.37 mmol) and potassium carbonate (641 mg, 4.64 mmol). The reaction mixture was heated in a Biotage Initiator™ Microwave Synthesizer at 190° C. for 6 hours. The mixture was filtered through a pad of Celite which was subsequently washed with ethyl acetate. The ethyl acetate solution was washed with water, dried over magnesium sulfate, filtered and then concentrated in vacuo. The product was purified by MDAP to yield the title compound (D3) (30 mg).

LC-MS: MH+=348 ($C_{22}H_{18}FNO_2$=347)

Description 4. 1-bromo-5-fluoro-2-nitro-4-[(phenylmethyl)oxy]benzene (D4)

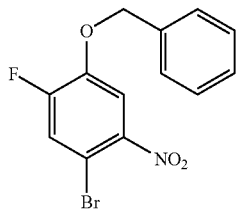

A mixture of 4-bromo-2-fluoro-5-nitrophenol (prepared according to WO2004/014361, 10 g, 42.3 mmol) and cesium carbonate (16.42 g, 50.4 mmol) in DMF (80 mL), was stirred at room temperature and treated with benzyl bromide (5.5 g, 46.5 mmol) and the mixture was stirred/sonicated at room temperature for 2 hours (~30 mins sonication). The DMF was evaporated and water and ethyl acetate were added and the product was extracted into ethyl acetate. The combined extracts were washed with sodium bicarbonate solution, dried ($Na_2SO_4$) and concentrated. Trituration of the solid with diethyl ether (3×) and drying gave the title compound (D4), (12.50 g).

NMR ($\delta_H$), ($CDCl_3$): 7.64 (1H, d, J=8.7 Hz), 7.48-7.35 (6H, series of m), 5.18 (2H, s).

Description 5. 7-bromo-5-fluoro-4-[(phenylmethyl)oxy]-1H-indole (D5)

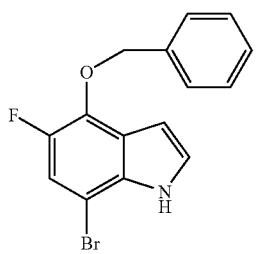

A solution of 1-bromo-5-fluoro-2-nitro-4-[(phenylmethyl)oxy]benzene (D4) (10.58 g, 32.4 mmol) in THF was cooled to −40° C. under argon and vinylmagnesium bromide (97 mL of 1M solution in THF, 97 mmol) was added quickly via syringe. The temperature reached ~−30° C. before cooling down to −40° C. The mixture was stirred at −40° C. for 40 mins and then quenched by the addition of $NH_4Cl$ solution. The mixture was allowed to reach room temperature and the layers were separated. The aqueous layer was reextracted with ethyl acetate and the combined organic layers were dried ($Na_2SO_4$) and evaporated. Chromatography on silica gel (elution with 0-50% ethyl acetate in hexane) gave the title compound as an orange oil (D5), (3.6 g).

LC-MS: MH+=320/322 ($C_{15}H_{11}BrFNO$=319/321)

Description 6. 7-bromo-5-fluoro-1-{3-fluoro-4-[(phenylmethyl)oxy]phenyl}-4-[(phenylmethyl)oxy]-1H-indole (D6)

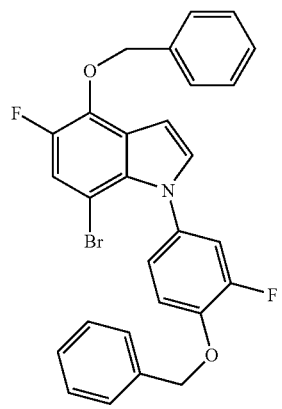

A mixture of 7-bromo-5-fluoro-4-[(phenylmethyl)oxy]-1H-indole (D5) (3 g, 9.37 mmol), {3-fluoro-4-[(phenylmethyl)oxy]phenyl}boronic acid (3.46 g, 14.06 mmol), copper (II) acetate (2.55 g, 14.06 mmol) and pyridine (0.834 mL, 0.815 g, 10.31 mmol) in dichloromethane (50 mL) were stirred together vigorously under an air atmosphere with powdered 4A molecular sieves (~10 g). After stirring for 20 hours, another 0.5 g of boronic acid were added and the mixture was stirred for a further 24 hours. Then another 1.73 g boronic acid (0.75 eq), copper acetate (1.28 g, 0.75 eq) and pyridine (1.52 mL, 2 eq) were added and stirring was continued at room temperature. After a further 24 hours, the reaction was diluted with ethyl acetate and filtered through celite. The celite was washed with ethyl acetate and the combined filtrates were washed with water (2×), dried ($Na_2SO_4$) and concentrated. Chromatography SP4 (0-30% ethyl acetate in hexane) gave the title compound as a white solid (D6), (1.463 g).

LC-MS: MH+=520/522 ($C_{28}H_{20}BrF_2NO_2$=519/521)

Description 7. 5-fluoro-1-{3-fluoro-4-[(phenylmethyl)oxy]phenyl}-4-[(phenylmethyl)oxy]-1H-indole (D7)

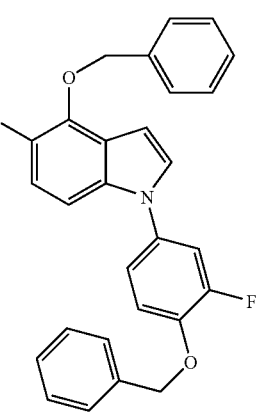

A solution of 7-bromo-5-fluoro-1-{3-fluoro-4-[(phenylmethyl)oxy]phenyl}-4-[(phenylmethyl)oxy]-1H-indole (D6) (400 mg, 0.769 mmol) in toluene (10 mL) was degassed by bubbling Argon through for a few minutes and tributylstannane (0.248 mL, 0.922 mmol) was added. The mixture was heated to reflux under argon and AIBN (~5 mg) was added and refluxing was continued. After 6 hours, another 0.124 mL of Bu$_3$SnH and a few crystals of AIBN were added and the mixture refluxed overnight—only a small amount of further reaction occurred therefore another 0.124 mL of Bu$_3$SnH and a few crystals of AIBN added and refluxing continued, again further reaction occurred but then stopped. Further quantities of Bu$_3$SnH (4×0.124 mL) together with a few crystals of AIBN were added at approx 2 hourly intervals. It was noticed that the reaction proceeded much more with thorough degassing with argon prior to addition of Bu$_3$SnH. After completion of the reaction (~48 hours total reaction), the toluene was evaporated and ether/20% aqueous ammonia were added. The product was extracted into ether and the extracts were washed with 20% aqueous ammonia (3×). The ether layer was dried over Na$_2$SO$_4$ and concentrated and the product was triturated with hexane to remove high Rf impurities. Chromatography on silica gel (elution with 0-15% diethyl ether in hexane) gave the title compound as a clear gum (D7), (143 mg).

LC-MS: MH$^+$=442 (C$_{28}$H$_{21}$F$_2$NO$_2$=441)

Description 8. 6-Ethenyl-4-(methyloxy)-1H-indole (D8)

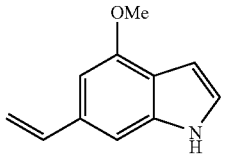

To a solution of 6-bromo-4-(methyloxy)-1H-indole (900 mg, 3.98 mmol) in 1,2-dimethoxyethane (20 mL) was added tributylvinyltin (1.74 mL, 5.96 mmol). The reaction mixture was degassed with argon and then treated with dichlorobis(tri-o-tolylphosphine)palladium (153 mg, 0.19 mmol). The mixture was heated at 90° C. for 65 hours. The mixture was filtered through a pad of celite, washed with ethyl acetate and then the filtrate concentrated in vacuo. The product was purified by silica gel chromatography eluting with 2-50% ethyl acetate in hexane to yield the title compound (D8), (781 mg).

LC-MS: MH$^+$=174 (C$_{11}$H$_{11}$NO=173)

Description 9. 6-Ethenyl-1-[3-fluoro-4-(methyloxy) phenyl]-4-(methyloxy)-1H-indole (D9)

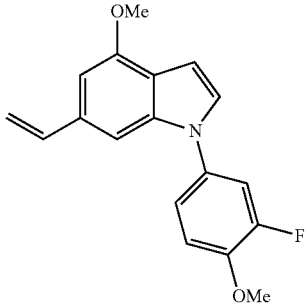

To a solution of 6-ethenyl-4-(methyloxy)-1H-indole (D8) (665 mg, 3.84 mmol) in dichloromethane (20 mL) was added 3-fluoro-4-methoxyphenylboronic acid (1.31 g, 7.71 mmol), triethylamine (1.1 mL, 7.91 mmol), copper (II) acetate (1.39 g, 7.68 mmol) and powdered 4A molecular sieves (1.0 g). The reaction mixture was stirred at room temperature in the presence of air for 18 hours. Further quantities of 3-fluoro-4-methoxyphenylboronic acid (330 mg), triethylamine (0.28 mL) and copper acetate (340 mg) were added and the mixture stirred at room temperature in the presence of air for a further 48 hours. The mixture was filtered and the solid washed with dichloromethane. The filtrate was concentrated at reduced pressure. The product was purified by silica gel chromatography eluting with 5-50% dichloromethane in hexane to yield the title compound (D9), (541 mg).

LC-MS: MH$^+$=298 (C$_{18}$H$_{16}$FNO$_2$=297)

Description 10. 6-Ethyl-1-[3-fluoro-4-(methyloxy) phenyl]-4-(methyloxy)-1H-indole (D10)

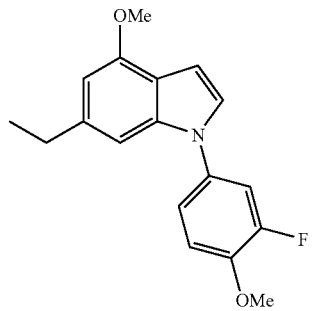

A solution of 6-ethenyl-1-[3-fluoro-4-(methyloxy)phenyl]-4-(methyloxy)-1H-indole (D9) (200 mg, 0.67 mmol) in ethanol (7 mL) and ethyl acetate (7 mL) was hydrogenated in an H-cube over a 10% palladium on charcoal catalyst. The resulting solution was concentrated and the product purified by silica gel chromatography eluting with 5-70% dichloromethane in hexane to yield the title compound (D10), (180 mg).

LC-MS: MH$^+$=300 (C$_{18}$H$_{18}$FNO$_2$=299)

Description 11. 7-Chloro-4-(methyloxy)-1H-indole (D11)

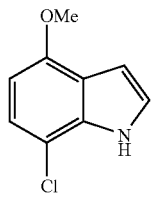

To a solution of 4-chloro-3-nitroanisole (6.0 g, 32.0 mmol) in tetrahydrofuran (140 mL) at −40° C. was added vinylmagnesium bromide (1M in tetrahydrofuran, 112 mL, 112.0 mmol). The mixture was stirred at −40° C. for 1.5 hours and then quenched by the addition of saturated aqueous ammonium chloride solution (150 mL). The reaction mixture was allowed to warm to room temperature and then the product extracted into ethyl acetate (×2). The combined organic layers were dried over magnesium sulphate, filtered and concentrated at reduced pressure. The product was purified by silica gel chromatography eluting with 2-15% ethyl acetate in hexane to yield the title compound (D11), (1.67 g).

LC-MS: MH$^+$=182 (C$_9$H$_8$ClNO=181)

Description 12. 7-Chloro-1-[3-fluoro-4-(methyloxy)phenyl]-4-(methyloxy)-1H-indole (D12)

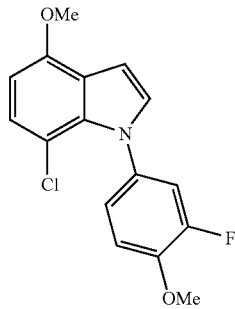

To a solution of 7-chloro-4-(methyloxy)-1H-indole (D11) (1.15 g, 6.35 mmol) in dichloromethane (20 mL) was added 3-fluoro-4-methoxyphenylboronic acid (2.2 g, 12.9 mmol), triethylamine (1.8 mL, 12.9 mmol), copper (II) acetate (2.3 g, 12.7 mmol) and powdered 4A molecular sieves (2.0 g). The reaction mixture was stirred at room temperature in the presence of air for 3 days. Further quantities of 3-fluoro-4-methoxyphenylboronic acid (440 mg), triethylamine (0.36 mL) and copper acetate (440 mg) were added and the mixture stirred at room temperature in the presence of air for a further 16 hours. The mixture was filtered and the solid washed with dichloromethane. The filtrate was concentrated at reduced pressure. The product was partially purified by silica gel chromatography eluting with 2-35% dichloromethane in hexane. The resulting product was partially dissolved in dimethylsulphoxide and acetonitrile. The undissolved solid was collected by filtration to yield the title compound (D12) (440 mg). The filtrate was concentrated at reduced pressure and the product purified by MDAP to yield a further batch of the title compound (D12), (143 mg).

LC-MS: MH$^+$=306 (C$_{16}$H$_{13}$ClFNO$_2$=305)

Description 13. 4-Bromo-1-{3-fluoro-4-[(phenylmethyl)oxy]phenyl}-1H-indole-6-carbonitrile (D13)

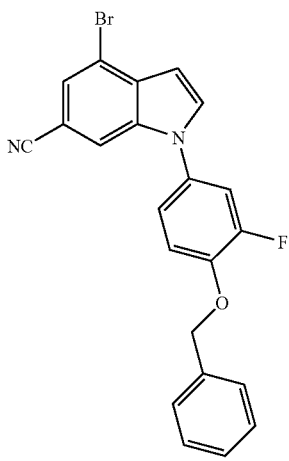

To a solution of 4-bromo-6-cyanoindole (900 mg, 4.1 mmol) in dichloromethane (30 mL) was added 4-benzyloxy-3-fluorobenzeneboronic acid (2.0 g, 8.1 mmol), triethylamine (1.2 mL, 8.6 mmol), copper (II) acetate (1.5 g, 8.2 mmol) and powdered 4A molecular sieves (2.0 g). The reaction mixture was stirred at room temperature in the presence of air for 16 hours. Further quantities of 4-benzyloxy-3-fluorobenzeneboronic acid (500 mg), triethylamine (0.3 mL) and copper acetate (375 mg) were added and the mixture stirred at room temperature in the presence of air for a further 16 hours. The mixture was filtered and the solid washed with dichloromethane. The filtrate was concentrated at reduced pressure. The product was purified by silica gel chromatography eluting with 2-40% ethyl acetate in hexane to yield the title compound (D13), (1.09 g).

NMR ($\delta_H$), (CDCl$_3$): 5.24 (2H, s), 6.80 (1H, dd J=3.3. 0.9 Hz), 7.14-7.23 (3H, m), 7.37-7.50 (6H, m), 7.57 (1H, d, J=1.1 Hz), 7.69 (1H, m).

Description 14. 1-{3-Fluoro-4-[(phenylmethyl)oxy]phenyl}-4-hydroxy-1H-indole-6-carbonitrile (D14)

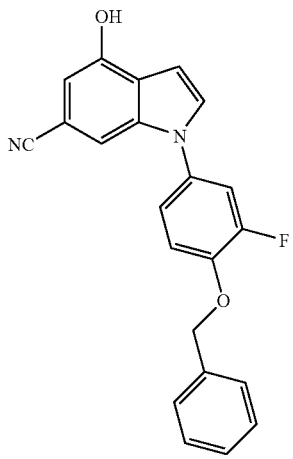

To a solution of 4-bromo-1-{3-fluoro-4-[(phenylmethyl)oxy]phenyl}-1H-indole-6-carbonitrile (D13) (400 mg, 0.95 mmol) in dioxane (6 mL) and water (6 mL) was added potassium hydroxide (216 mg, 3.9 mmol). The reaction mixture was degassed with argon and then treated with 2-di-tert-butylphosphino-2',4',6'-trisisopropylbiphenyl (22 mg, 0.05 mmol) and tris(dibenzylideneacetone)dipalladium (0) (19 mg, 0.02 mmol). After heating at 85° C. for 1 hour, the mixture was allowed to cool to room temperature and then diluted with ethyl acetate and water. The pH was adjusted to 7 by the addition of 1M hydrochloric acid. The organic phase was dried over magnesium sulphate, filtered and concentrated in vacuo. The product was purified by silica gel chromatography eluting with 2-60% ethyl acetate in hexane to yield the title compound (D14), (323 mg).

LC-MS: MH$^+$=359 (C$_{22}$H$_{15}$FN$_2$O$_2$=358)

Description 15. (E)-2-(2-bromo-4-fluoro-6-nitrophenyl)-N,N-dimethylethenamine (D15)

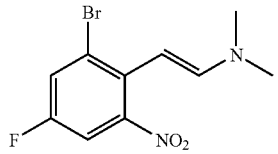

To a solution of 1-bromo-5-fluoro-2-methyl-3-nitrobenzene (5.0 g, 21.37 mmol) in N,N-dimethylformamide (50 mL) was added N,N-dimethylformamide dimethyl acetal (8.58 mL, 64.1 mmol) and pyrrolidine(1.767 mL, 21.37 mmol). The reaction mixture was heated at 110° C. for 4 hours. After cooling to room temperature, the N,N-dimethylformamide was removed by evaporation. The residue was taken up in diethyl ether and water. After separation of the organic layer, the aqueous layer was re-extracted with diethyl ether. The combined organic layers were dried over magnesium sulphate, filtered and concentrated to give a red/brown oil which was used directly in the following reaction without purification.

Description 16. 4-Bromo-6-fluoro-1H-indole (D16)

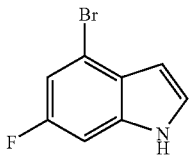

To a solution of crude[(E)-2-(2-bromo-4-fluoro-6-nitrophenyl)ethenyl]dimethylamine (D15) (6.07 g, 21.0 mmol) in acetic acid (200 mL) and water (50.0 mL) at 75° C. was added zinc powder (15.11 g, 231 mmol) portionwise over 1 hour. The mixture was heated to 85° C. and stirred for 4 hours. After cooling to room temperature, the reaction mixture was neutralised by the addition of 50% aqueous sodium hydroxide solution. The product was extracted into diethyl ether. After separation of the layers, the aqueous phase was re-extracted with diethyl ether. The combined organic layers were dried over magnesium sulphate, filtered and concentrated. The product was partially purified by silica gel chromatography eluting with 5-30% ethyl acetate in hexane. Purer fractions were combined to give the title compound (D16), (580 mg).

LC-MS: [M-H]$^-$=212, 214 (C$_8$H$_5$BrFN=213, 215)

Description 17. 4-Bromo-6-fluoro-1-{3-fluoro-4-[(phenylmethyl)oxy]phenyl}-1H-indole (D17)

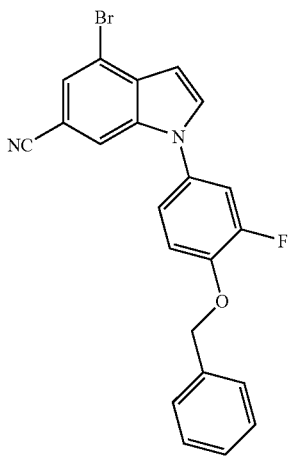

To a solution of 4-bromo-6-fluoro-1H-indole (D16) (580 mg, 2.71 mmol) in dichloromethane (20 mL) was added {3-fluoro-4-[(phenylmethyl)oxy]phenyl}boronic acid (1.33 g, 5.42 mmol), copper (II) acetate (984 mg, 5.42 mmol), triethylamine (0.755 mL, 5.42 mmol) and powdered 4A molecular sieves (2 g, 2.71 mmol). The mixture was stirred at room temperature in the presence of air for 3 days. The reaction was filtered through a pad of celite and washed with dichloromethane. The organic solution was washed with water and then the aqueous phase re-extracted with dichloromethane. The combined organic phases were dried over magnesium sulphate, filtered and concentrated. The product was partially purified by silica gel chromatography eluting with 5-20% ethyl acetate in hexane to yield the title compound (D17), (980 mg).

LC-MS: MH$^+$=414, 415 (C$_{21}$H$_{14}$BrF$_2$NO=413, 415)

Description 18. 6-Fluoro-1-{3-fluoro-4-[(phenylmethyl)oxy]phenyl}-1H-indol-4-ol (D18)

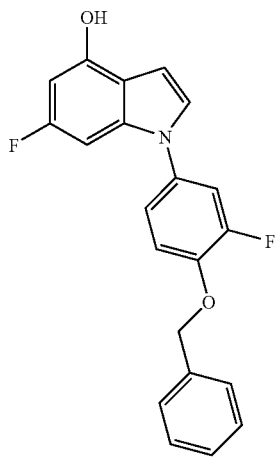

To a solution of 4-bromo-6-fluoro-1-{3-fluoro-4-[(phenylmethyl)oxy]phenyl}-1H-indole (D17) (980 mg, 2.366 mmol) in 1,4-dioxane (20 mL) and water (20 mL) was added potassium hydroxide (531 mg, 9.46 mmol). The reaction mixture was purged with argon and then treated with 2-di-tert-butylphosphino-2',4',6'-triisopropylbiphenyl (60.3 mg, 0.142 mmol) and tris(dibenzylideneacetone)dipalladium(0) (43.3 mg, 0.047 mmol). The reaction mixture was heated at 90° C. for 1 hour. After cooling to room temperature, the mixture was diluted with ethyl acetate and water. The pH was adjusted to ~7 by the addition of 1M hydrochloric acid. After separation of the layers, the aqueous phase was re-extracted with ethyl acetate. The combined organic layers were dried over magnesium sulphate, filtered and concentrated. The product was purified by silica gel chromatography eluting with 5-40% ethyl acetate in hexane to yield the title compound (D18), (382 mg).

LC-MS: MH$^+$=352 (C$_{21}$H$_{15}$F$_2$NO$_2$=351)

Description 19. 4-bromo-6-fluoro-1-{4-[(phenylmethyl)oxy]phenyl}-1H-indole (D19)

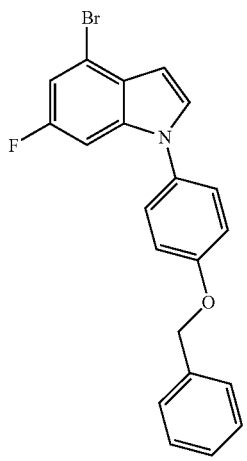

A mixture of 4-bromo-6-fluoro-1H-indole (D16), (200 mg, 0.935 mmol), 4-benzyloxyphenylboronic acid (426 mg, 1.87 mmol), copper (II) acetate (332 mg, 1.87 mmol) and triethylamine (0.26 mL, 188 mg, 1.87 mmol) in dichloromethane (5 mL) was stirred in air at room temperature for 16 hours. The mixture was filtered through celite, concentrated and purified by chromatography on silica gel (elution with 0-20% ethyl acetate in hexanes) to give the title compound as a pink solid (D19), (205 mg).

LC-MS: MH$^+$=396/398 (C$_{21}$H$_{15}$BrFNO=395/397)

Description 20. 6-fluoro-1-{4-[(phenylmethyl)oxy]phenyl}-1H-indol-4-ol (D20)

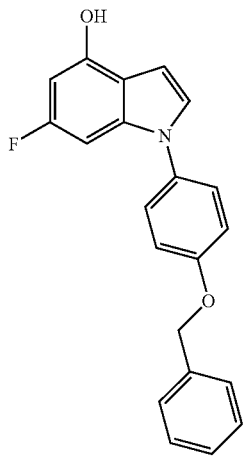

A mixture of 4-bromo-6-fluoro-1-{4-[(phenylmethyl)oxy]phenyl}-1H-indole (D19) (200 mg, 0.505 mmol) and potassium hydroxide (113 mg, 2.02 mmol) in 1,4-dioxan (3 mL)/water (3 mL) was treated with Pd$_2$dba$_3$ (9 mg, 0.02 mmol) and phosphine ligand, bis(1,1-dimethylethyl)[2',4',6'-tris(1-methylethyl)-2-biphenylyl]phosphane (11 mg, 0.05 mmol) and the mixture was heated to 85° C. for 1.5 hours. After cooling, the mixture was diluted with dichloromethane and water and the product was extracted into dichloromethane. The combined organic layers were dried (MgSO$_4$) and evaporated. Chromatography on silica gel (elution with 0-50% ethyl acetate in hexane) gave the title compound (D20), (75 mg).

LC-MS: MH$^+$=334 (C$_{21}$H$_{16}$FNO$_2$=333)

Description 21. 1-{3,5-difluoro-4-[(phenylmethyl)oxy]phenyl}-4-[(phenylmethyl)oxy]-1H-indole (D21)

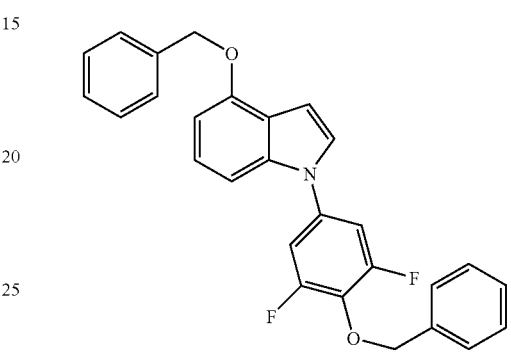

a) 4-bromo-2,6-difluorophenol (2 g, 9.57 mmol) was dissolved in DMF (19 mL) and to this was added Cs$_2$CO$_3$ (4.37 g, 13.34 mmol) and the solution was stirred for 15 minutes before benzyl bromide (1.64 g, 9.57 mmol) was added. After 2 hours at room temperature the mixture was partitioned between ethyl acetate (100 mL)/water (100 mL), the layers were separated and the aqueous extracted with ethyl acetate (100 mL). The combined organics were washed with brine (2×50 mL) and water (2×50 mL) and dried over MgSO$_4$. The crude material (2.67 g) was filtered through a pad of silica and eluted with hexane to afford 4-bromo-2,6-difluorophenyl phenylmethyl ether after evaporation of the solvent (2.38 g, 83%).

NMR (δ$_H$), (CDCl$_3$): 7.3-7.45 (5H, m), 7.0-7.1 (2H, m), 5.14 (2H, s)

b) 4-[(phenylmethyl)oxy]-1H-indole (500 mg, 2.24 mmoL), 4-bromo-2,6-difluorophenyl phenylmethyl ether (prepared as described in part a), 559 mg, 1.87 mmoL), K$_3$PO$_4$ (990 mg, 4.67 mmoL) and L-Proline (43 mg, 0.373 mmoL) were dissolved in DMF (5 mL) in a microwave vial and degassed by sonication under a flow of argon. To this was added CuI (71 mg, 0.373 mmoL) and the solution was heated to 140° C. in the microwave reactor. After 3 hours the mixture was partitioned between ethyl acetate (100 mL)/water (100 mL), the phases were separated and the aqueous phase re-extracted with ethyl acetate (100 mL). The combined organic phases were washed with sat. NH$_4$Cl (2×100 mL), water (100 mL) and brine (2×100 mL) and finally dried over MgSO$_4$. The crude product was purified by flash chromatography (Biotage SP4, 40+S Cartridge) eluting with a gradient of 0 to 20% Et$_2$O in hexane to give the title compound (D21), (299 mg).

LC-MS: MH$^+$=442 (C$_{28}$H$_{21}$F$_2$NO$_2$=441)

Description 22. 1-{2,5-difluoro-4-[(phenylmethyl)oxy]phenyl}-4-[(phenylmethyl)oxy]-1H-indole (D22)

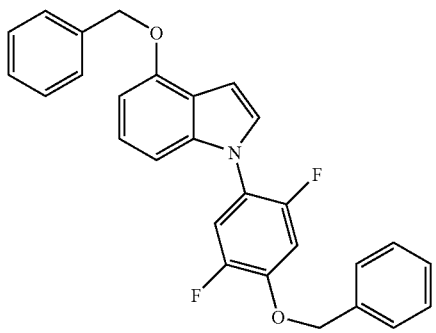

a) 4-bromo-2,5-difluorophenol (2 g, 9.57 mmol) was dissolved in DMF (19 mL) and to this was added Cs$_2$CO$_3$ (4.37 g, 13.34 mmol) and the solution was stirred for 15 minutes before benzyl bromide (1.64 g, 9.57 mmol) was added. After 1 hour at room temperature the mixture was partitioned between ethyl acetate (100 mL)/water (100 mL), the layers were separated and the aqueous extracted with ethyl acetate. The combined organics were washed with saturated NH$_4$Cl (100 mL), water (100 mL) and brine (2×100 mL) and dried over MgSO$_4$. The crude material (2.74 g) was filtered through a pad of silica and eluted with 20% Et$_2$O in hexane to afford 4-bromo-2,5-difluorophenyl phenylmethyl ether after evaporation of the solvent (2.51 g, 88%).

NMR ($\delta_H$), (CDCl$_3$): 7.3-7.45 (5H, m), 7.25-7.29 (1H, dd), 6.78-6.82 (1H, dd), 5.1 (2H, s).

b) In two microwave vials were placed 4-[(phenylmethyl)oxy]-1H-indole (500 mg, 2.24 mmol), 4-bromo-2,5-difluorophenyl phenylmethyl ether (prepared as described in part a), 559 mg, 1.87 mmol), K$_3$PO$_4$ (990 mg, 4.67 mmol), L-Proline (43 mg, 0.373 mmol) and DMF (5 mL) and the mixture was degassed by sonication under a flow of argon. To each vial was added CuI (71 mg, 0.373 mmol) and the solutions were heated to 140° C. in the microwave reactor. After 4 hours a second portion of L-Proline (43 mg, 0.373 mmol) was added and heated for an additional hour. The two mixtures were partitioned between ethyl acetate (100 mL)/water (100 mL), the phases were separated and the aqueous phase re-extracted with ethyl acetate (100 mL). The combined organic phases were washed with sat. NH$_4$Cl (2×100 mL), water (100 mL) and brine (2×100 mL) and finally dried over MgSO$_4$. The combined crude materials were purified by flash chromatography (Biotage SP4, 40+M Cartridge) eluting with a gradient of 0 to 30% Et$_2$O in hexane to give the title compound (D22), (258 mg).

NMR ($\delta_H$), (CDCl$_3$): 7.3-7.6 (11H, m), 7.12 (2H, m), 6.92 (2H, m), 6.85 (1H, dd), 6.65 (1H, d), 5.25 (2H, s), 5.20 (2H, s)

Description 23. 1-{2,3-difluoro-4-[(phenylmethyl)oxy]phenyl}-4-[)phenylmethyl)oxy]-1H-indole ((D23)

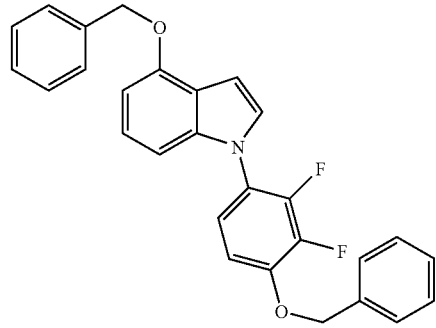

4-[(phenylmethyl)oxy]-1H-indole (432 mg, 1.94 mmoL), 4-bromo-2,3-difluorophenyl phenylmethyl ether (486 mg, 1.63 mmoL), K$_3$PO$_4$ (863 mg, 4.06 mmoL) and L-Proline (38 mg, 0.329 mmoL) were dissolved in DMF (5 mL) in a microwave vial and degassed by sonication under a flow of argon for 5 minutes. To this was added CuI (62.7 mg, 0.329 mmoL) and the solution was heated to 140° C. in the microwave reactor. After 6 hours a second portion of CuI (62.7 mg, 0.329 mmoL) and L-Proline (38 mg, 0.329 mmoL) were added and heated for 2 more hours. The mixture was partitioned between ethyl acetate (75 mL)/water (75 mL), the phases were separated and the aqueous phase re-extracted with ethyl acetate (3×75 mL). The combined organic phases were washed with sat. NH$_4$Cl (2×75 mL), water (75 mL) and brine (2×75 mL) and finally dried over MgSO$_4$. The crude product was purified by flash chromatography (Biotage SP4, 40+S Cartridge) eluting with a gradient of 0 to 30% Et$_2$O in hexane and then further purified by MDAP to give the title compound (D23), (142 mg).

LC-MS: MH$^+$=442 (C$_{28}$H$_{21}$F$_2$NO$_2$=441)

Description 24. 4-[(phenylmethyl)oxy]-1-{4-[(phenylmethyl)oxy]phenyl}-1H-indole (D24)

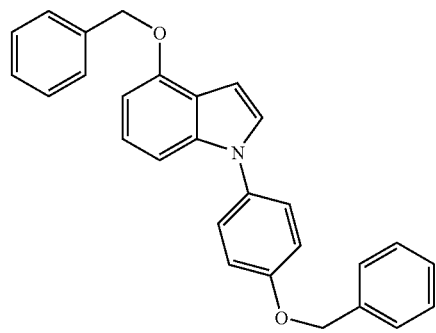

4-[(phenylmethyl)oxy]-1H-indole (504 mg, 2.26 mmoL), 4-bromophenyl phenylmethyl ether (580 mg, 1.88 mmoL), K$_3$PO$_4$ (998 mg, 4.7 mmoL) and L-Proline (43.3 mg, 0.376 mmoL) were dissolved in 1,4-Dioxane (4 mL) in a microwave vial and degassed by sonication under a flow of argon. To this was added CuI (18 mg, 0.094 mmoL) and the solution was heated to 100° C. in the microwave reactor. After 5 hours a second portion of CuI (48 mg, 0.252 mmoL) and L-Proline (40 mg, 0.347 mmoL) were added and the mixture heated for 2 more hours. The reaction mixture was filtered through a pad of celite and concentrated. The residue was partitioned between ethyl acetate (100 mL)/water (100 mL), the phases were separated and the aqueous phase re-extracted with ethyl acetate (100 mL). The combined organic phases were washed with brine (2×50 mL) then water (50 mL) and finally dried over MgSO$_4$. The crude product was purified by flash chromatography (Biotage SP4) eluting with a gradient of 0 to 30% Et$_2$O in hexane to give the title compound (D24), (143 mg).

LC-MS: MH$^+$=442 (C$_{28}$H$_{21}$F$_2$NO$_2$=441)

Example 1

1(3-Fluoro-4-hydroxyphenyl)-1H-indol-4-ol (E1)

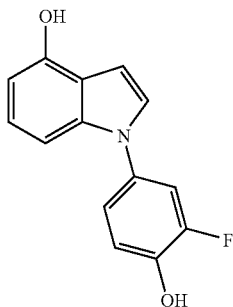

A suspension of 1-{3-fluoro-4-[(phenylmethyl)oxy]phenyl}-4-[(phenylmethyl)oxy]-1H-indole (D1) (2.32 g, 5.48 mmol) in ethanol (100 mL) and ethyl acetate (100 mL) was hydrogenated in the presence of 10% Pd on charcoal (500 mg) at atmospheric pressure and room temperature overnight. The mixture was filtered and concentrated and then purified by chromatography on silica gel (elution with 0-50% ethyl acetate in hexane) to give a pink gum, which was solidified by the addition of chloroform (~0.5 mL) and hexane. The product was collected by filtration and washed with hexane to give an off white powder. This product was dissolved in methanol and passed through an SCX cartridge (to trap a trace of indoline formed in the reaction) and the cartridge was eluted with methanol. The product containing fractions were concentrated and then triturated with hexane and dried to give the title compound (E1) as an off-white solid (905 mg).

LC-MS: MH$^+$=244 (C$_{14}$H$_{10}$FNO$_2$=243)

NMR ($\delta_H$), (CDCl$_3$): 6.47 (1H, d, J=7.4 Hz), 6.68 (1H, d, J=3.3 Hz), 6.93 (1H, d, J=8.3 Hz), 6.96 (1H, dd, J=7.6, 8.2 Hz), 7.10 (1H, dd, J=8.4, 9.4 Hz), 7.19 (1H, ddd, J=0.9, 2.6, 8.6 Hz), 7.36 (1H, d, J=3.3 Hz), 7.37 (1H, dd, J=2.6, 11.9 Hz), 9.56 (1H, broad s), 10.09 (1H, broad s).

Example 2

1-(3-Fluoro-4-hydroxyphenyl)-3-methyl-1H-indol-4-ol (E2)

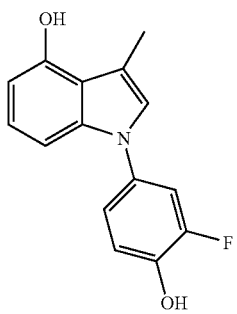

A solution of 2-fluoro-4-{3-methyl-4-[(phenylmethyl)oxy]-1H-indol-1-yl}phenol (D2) (140 mg, 0.40 mmol) in ethanol (20 mL) was hydrogenated in an H-cube over a 10% Pd/C catalyst. The resulting solution was concentrated and the product purified by silica gel chromatography eluting with 5-50% ethyl acetate in hexane to yield the title compound (E2) (47 mg).

LC-MS: MH$^+$=258 (C$_{15}$H$_{12}$FNO$_2$=257)

Example 3

1-(3-Fluoro-4-hydroxyphenyl)-2-methyl-1H-indol-4-ol (E3)

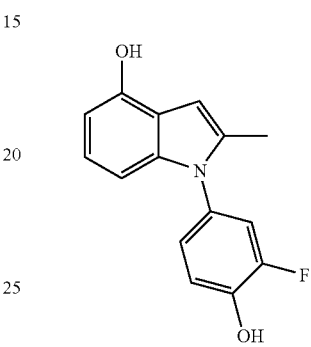

To a solution of 2-fluoro-4-{2-methyl-4-[(phenylmethyl)oxy]-1H-indol-1-yl}phenol (D3) (85 mg, 0.24 mmol) in ethanol (7 mL) was added a solution of tetra-n-butylammonium chloride (170 mg, 0.61 mmol) in ethyl acetate (1 mL). The solution was hydrogenated in an H-cube over a 10% Pd/C catalyst. The resulting solution was concentrated and the product purified by MDAP to yield the title compound (E3) (31 mg).

LC-MS: MH$^+$=258 (C$_{15}$H$_{12}$FNO$_2$=257)

Example 4

7-bromo-5-fluoro-1-(3-fluoro-4-hydroxyphenyl)-1H-indol-4-ol (E4)

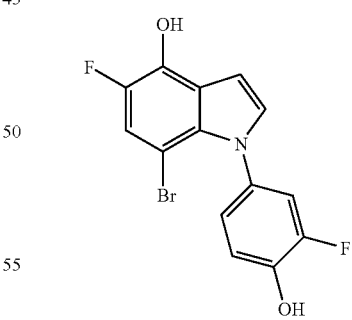

The 7-bromo-5-fluoro-1-{3-fluoro-4-[(phenylmethyl)oxy]phenyl}-4-[(phenylmethyl)oxy]-1H-indole (D6) (442 mg, 0.849 mmol) in ethyl acetate (20 mL) was hydrogenated in the H-cube over 10% Pd—C at a flow rate of 1 mL/min. The product mixture was evaporated and chromatographed (silica gel, ethyl acetate in hexane) to give material that was further purified by MDAP to give the title compound (E4) as an off white solid. (84 mg)

LC-MS: MH$^+$=340/342 (C$_{14}$H$_{18}$BrF$_2$NO$_2$=339/341)

Example 5

5-fluoro-1-(3-fluoro-4-hydroxyphenyl)-1H-indol-4-ol (E5)

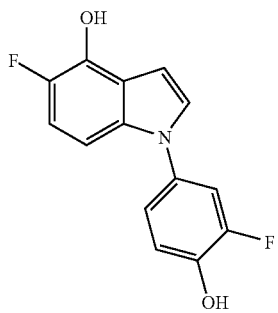

A solution of 5-fluoro-1-{3-fluoro-4-[(phenylmethyl)oxy]phenyl}-4-[(phenylmethyl)oxy]-1H-indole (D7) (143 mg) in ethyl acetate (8 mL) was passed through the H-cube at 1 mL/min with 1 Bar $H_2$ pressure. The solution was evaporated and purified by chromatography on silica gel (elution with 0-50% ethyl acetate in hexane) to give the title compound (E5) as an off white solid (65 mg).

LC-MS: $MH^+$=262 ($C_{14}H_9F_2NO_2$=261)

Example 6

6-Ethyl-1-(3-fluoro-4-hydroxyphenyl)-1H-indol-4-ol (E6)

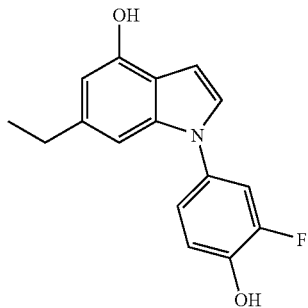

To a solution of 6-ethyl-1-[3-fluoro-4-(methyloxy)phenyl]-4-(methyloxy)-1H-indole (D10) (180 mg, 0.60 mmol) in dichloromethane (6 mL) at −78° C. was added boron tribromide (1 M solution in dichloromethane, 2.5 mL, 2.5 mmol). The reaction mixture was allowed to warm to 0° C. and then quenched by the addition of water and dichloromethane. The solution was neutralised by the addition of dilute sodium hydrogen carbonate solution. The organic phase was separated and then the aqueous phase re-extracted with ethyl acetate. The combined organic phases were dried over magnesium sulphate, filtered and concentrated at reduced pressure. The product was purified by MDAP to yield the title compound (E6), (8 mg).

LC-MS: $MH^+$=272 ($C_{16}H_{14}FNO_2$=271)

Example 7

7-Chloro-1-(3-fluoro-4-hydroxyphenyl)-1H-indol-4-ol (E7)

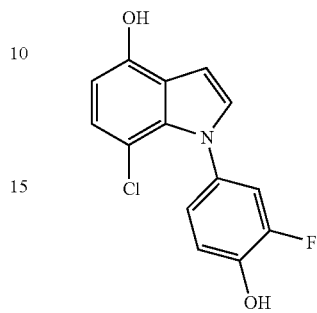

To a solution of 7-chloro-1-[3-fluoro-4-(methyloxy)phenyl]-4-(methyloxy)-1H-indole (D12) (533 mg, 1.75 mmol) in dichloromethane (50 mL) at −78° C. was added boron tribromide (1M solution in dichloromethane, 7 mL, 7.0 mmol). The reaction mixture was allowed to warm to room temperature and then quenched by the addition of methanol and then water and dichloromethane. After separation of the layers, the aqueous phase was re-extracted with dichloromethane. The combined organic layers were dried over magnesium sulphate, filtered and concentrated at reduced pressure. The product was partially purified by silica gel chromatography eluting with 5-70% ethyl acetate in hexane. The product was further purified by MDAP to yield the title compound (E7), (39 mg).

LC-MS: $MH^+$=278 ($C_{14}H_9ClFNO_2$=277)

Example 8

1-(3-Fluoro-4-hydroxyphenyl)-4-hydroxy-1H-indole-6-carbonitrile (E8)

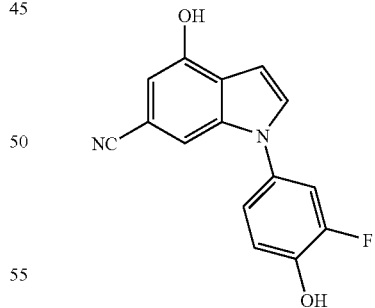

A solution of 1-{3-fluoro-4-[(phenylmethyl)oxy]phenyl}-4-hydroxy-1H-indole-6-carbonitrile (D14) (320 mg, 0.89 mmol) in ethanol (25 mL) and ethyl acetate (5 mL) was hydrogenated in an H-cube over a 10% palladium on charcoal catalyst. The resulting solution was concentrated and the product purified by silica gel chromatography eluting with 2-60% ethyl acetate in hexane to yield the title compound (E8), (175 mg).

LC-MS: $MH^+$=269 ($C_{15}H_9FN_2O_2$=268)

Example 9

6-Fluoro-1-(3-fluoro-4-hydroxyphenyl)-1H-indol-4-ol (E9)

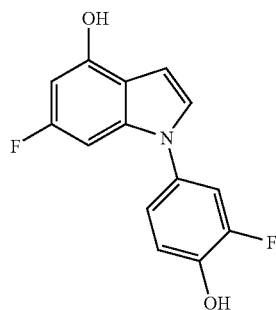

A solution of 6-fluoro-1-{3-fluoro-4-[(phenylmethyl)oxy]phenyl}-1H-indol-4-ol (D18) (380 mg, 1.082 mmol) in ethyl acetate (30 mL) was hydrogenated in an H-cube over a 10% palladium on charcoal catalyst. The resulting solution was concentrated. The product was purified by silica gel chromatography eluting with 10-100% ethyl acetate in hexane to yield the title compound (E9), (213 mg).

LC-MS: MH$^+$=262 (C$_{14}$H$_9$F$_2$NO$_2$=261)

Example 10

6-fluoro-1-(4-hydroxyphenyl)-1H-indol-4-ol (E10)

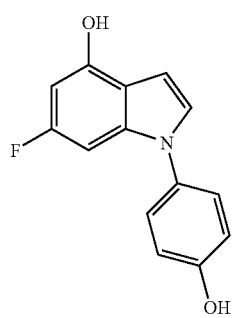

A mixture of 6-fluoro-1-{4-[(phenylmethyl)oxy]phenyl}-1H-indol-4-ol (D20) (75 mg) and palladium on charcoal (75 mg) in ethanol (3 mL) was stirred under hydrogen at room temperature for 3 hours. The mixture was filtered and the filtrate was evaporated and chromatographed on silica gel (0-50% ethyl acetate in hexane). The product containing fractions were concentrated and then re-evaporated from ether (3×) to give the title compound (E10) as a white solid, (15 mg).

LC-MS: [M-H]$^-$=242 (C$_{14}$H$_{10}$FNO$_2$=243)

Example 11

1-(3,5-difluoro-4-hydroxyphenyl)-1H-indol-4-ol (E11)

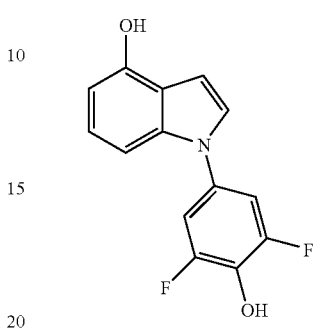

1-{3,5-difluoro-4-[(phenylmethyl)oxy]phenyl}-4-[(phenylmethyl)oxy]-1H-indole (D21) (299 mg, 0.678 mmoL) was dissolved in ethyl acetate (10 mL) and was hydrogenated at room temperature and atmospheric pressure in the presence of 10% palladium on charcoal (50% wet) (150 mg). After 21 hours the mixture was filtered and concentrated in vacuo. The crude product was purified by flash chromatography (Biotage SP4) eluting with a gradient of 0 to 100% Et$_2$O in hexane to give the title compound (E11), (61 mg).

LC-MS: MH$^+$=262 (C$_{14}$H$_9$F$_2$NO$_2$=261)

Example 12

1-(2,5-difluoro-4-hydroxyphenyl)-1H-indol-4-ol (E12)

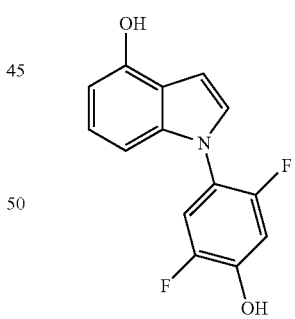

1-{2,5-difluoro-4-[(phenylmethyl)oxy]phenyl}-4-[(phenylmethyl)oxy]-1H-indole (D22) (258 mg, 0.584 mmoL)) was dissolved in ethyl acetate (10 mL) and was hydrogenated at room temperature and atmospheric pressure in the presence of 10% palladium on charcoal (50% wet) (120 mg). After 22 hours the mixture was filtered and concentrated in vacuo. The crude product was purified by MDAP to give the title compound (E12), (114 mg).

LC-MS: MH$^+$=262 (C$_{14}$H$_9$F$_2$NO$_2$=261)

Example 13

1-(2,3-difluoro-4-hydroxyphenyl)-1H-indol-4-ol (E13)

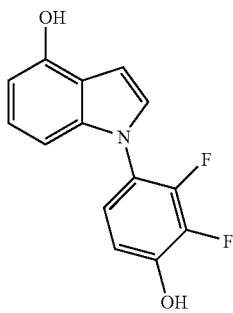

1-{2,3-difluoro-4-[(phenylmethyl)oxy]phenyl}-4-[(phenylmethyl)oxy]-1H-indole (D23) (141 mg, 0.319 mmoL) was dissolved in ethyl acetate (10 mL) and was hydrogenated at room temperature and atmospheric pressure in the presence of 10% palladium on charcoal (50% wet) (70 mg). After 22 hours the mixture was filtered and concentrated in vacuo. The crude product was purified by MDAP and the isolated material was partitioned between ethyl acetate and sat. $NH_4Cl$. The phases were separated and the aqueous phase extracted with more ethyl acetate. The combined organic phases were washed with brine, dried over $MgSO_4$, filtered and concentrated to afford the title compound (E13), (45 mg).

LC-MS: $MH^+$=262 ($C_{14}H_9F_2NO_2$=261)

Example 14

1-(4-hydroxyphenyl)-1H-indol-4-ol (14)

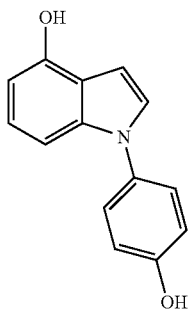

4-[(phenylmethyl)oxy]-1-{4-[(phenylmethyl)oxy]phenyl}-1H-indole (D24) (143 mg, 0.352 mmoL) was dissolved in ethyl acetate (10 mL) and was hydrogenated at room temperature and atmospheric pressure in the presence of 10% palladium on charcoal (50% wet) (70 mg). After 28 hours the mixture was filtered and concentrated in vacuo. The crude product was purified by flash chromatography (Biotage SP4) eluting with a gradient of 0 to 100% ethyl acetate in hexane to give the title compound (E14), (55 mg).

LC-MS: $MH^+$=226 ($C_{14}H_{11}NO_2$=225)

It is to be understood that the present invention covers all combinations of particular and preferred subgroups described herein above.

Assays for Determining Biological Activity

Assay Buffer (AB) (50 mM MOPES pH 7.5, 50 mM NaF, 2.5 mM CHAPs), in deionized water, 5 mM 1,4 dithiothreitol (DTT) added on day of the experiment. The appropriate amount of AB was placed in a plastic tube, adding solid DTT before the assay was run. AB with DTT was distributed to plastic tubes. We have found use of plastic to be important vs glass. A final concentration of 6 nM ERbeta protein was added to the tube followed by gentle inversion. A final concentration of 1.5 nM ER FP ligand (Fluormone™ EL Red 200 nM in 20 mM Tris, 90% Methanol purchased from Invitrogen catalogue no P3030) was added to the same tube followed by gentle inversion. This was allowed to sit for 5-10 minutes before adding it to the 384 assay plate. Similar protocol was used for ERalpha with a final concentration of 4 nM ERalpha and 1.5 nM ER FP ligand.

384 plates containing test compounds dissolved in 100% DMSO at 1 mM were serially diluted (1:3) by a Beckman FX. Serial diluted test compounds were added, 0.1 µL, to the assay plates with a maximum final concentration of 10 uM. Once the assay plates were ready, 10 µL of the above reagents were added to the appropriate set of plates with the Thermo combi. These plates were then sealed and place at room temperature for 3 hours.

The plates were then placed on the Molecular Devices Analyst and counted (excitation 535 nm, emission 590 nm with a 561 Dichroic mirror). Data was normalized to control then fitted to a non-linear least squares algorithm (see below).

pIC50 Calculation $$y=a+((b-a)/(1+(10^x/10^c)\hat{0}d)$$

Results

The compounds of Examples 1 to 14 had a $pIC_{50}$>6 in the ER beta FP binding assay. The compounds of Examples 4, 5, 7, 8, 9 and 10 had a $pIC_{50}$>8 in the ER beta FP binding assay. Certain compounds also had selectivity>10 fold versus ER alpha.

The amino acid sequence of human ER beta used in this assay is

```
MKKHHHHHHG ELLLDALSPE QLVLTLLEAE PPHVLISRPS

APFTEASMMM SLTKLADKEL VHMISWAKKI PGFVELSLFD

QVRLLESCWM EVLMMGLMWR SIDHPGKLIF APDLVLDRDE

GKCVEGILEI FDMLLATTSR FRELKLQHKE YLCVKAMILL

NSSMYPLVTA TQDADSSRKL AHLLNAVTDA LVWVIAKSGI

SSQQQSMRLA NLLMLLSHVR HASNKGMEHL LNMKCKNVVP

VYDLLLEMLN AHVLRGCKSS ITGSECSPAE DSKSKEGSQN

PQSQ
```

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation the following claims:

The invention claimed is:
1. A compound of formula (I):

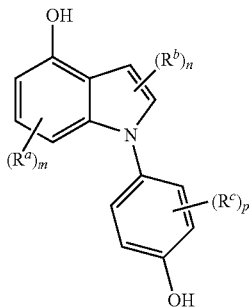

wherein $R^a$, $R^b$ and $R^c$ are independently selected from halo, $C_{1-4}$alkoxy, $C_{1-4}$alkyl, $C_{2-4}$alkenyl, $C_{1-5}$alkanoyl, $CF_3$, $CF_3O$ and cyano;
m is zero or an integer from 1 to 3;
n is zero or an integer 1 or 2;
p is zero or an integer from 1 to 4;
however m, n and p together equal 5 or less;
or a pharmaceutically acceptable salt thereof.

2. A pharmaceutical composition comprising a compound or salt according to claim 1 together with a pharmaceutical carrier and/or excipient.

3. A compound or salt according to claim 1 selected from the compounds:
 1-(3-Fluoro-4-hydroxyphenyl)-1H-indol-4-ol;
 1-(3-Fluoro-4-hydroxyphenyl)-3-methyl-1H-indol-4-ol;
 1-(3-Fluoro-4-hydroxyphenyl)-2-methyl-1H-indol-4-ol;
 7-bromo-5-fluoro-1-(3-fluoro-4-hydroxyphenyl)-1H-indol-4-ol;
 5-fluoro-1-(3-fluoro-4-hydroxyphenyl)-1H-indol-4-ol;
 6-Ethyl-1-(3-fluoro-4-hydroxyphenyl)-1H-indol-4-ol;
 7-Chloro-1-(3-fluoro-4-hydroxyphenyl)-1H-indol-4-ol;
 1-(3-Fluoro-4-hydroxyphenyl)-4-hydroxy-1H-indole-6-carbonitrile;
 6-Fluoro-1-(3-fluoro-4-hydroxyphenyl)-1H-indol-4-ol;
 6-fluoro-1-(4-hydroxyphenyl)-1H-indol-4-ol;
 1-(3,5-difluoro-4-hydroxyphenyl)-1H-indol-4-ol;
 1-(2,5-difluoro-4-hydroxyphenyl)-1H-indol-4-ol;
 1-(2,3-difluoro-4-hydroxyphenyl)-1H-indol-4-ol; and
 1-(4-hydroxyphenyl)-1H-indol-4-ol;
or a pharmaceutically acceptable salt thereof.

* * * * *